US007593554B2

(12) United States Patent
Miller et al.

(10) Patent No.: US 7,593,554 B2
(45) Date of Patent: Sep. 22, 2009

(54) SYSTEM AND METHOD FOR COMPARING ULTRASOUND IMAGES CORRESPONDING TO TWO USER-SELECTED DATA POINTS

(75) Inventors: Edward A. Miller, Everett, WA (US); Rohit Garg, Seattle, WA (US); Damien Dolimier, Bothell, WA (US); Danny M. Skyba, Bothell, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 751 days.

(21) Appl. No.: 10/264,029

(22) Filed: Oct. 3, 2002

(65) Prior Publication Data

US 2004/0066957 A1 Apr. 8, 2004

(51) Int. Cl.
 *G06K 9/00* (2006.01)
(52) U.S. Cl. ..................................... 382/128
(58) Field of Classification Search ................. 382/128
 See application file for complete search history.

(56) References Cited

U.S. PATENT DOCUMENTS

| | | | |
|---|---|---|---|
| 5,860,931 A * | 1/1999 | Chandler ................... 600/458 |
| 6,319,204 B1 * | 11/2001 | Brock-Fisher et al. ...... 600/458 |
| 6,558,328 B2 * | 5/2003 | Rubin et al. ................ 600/447 |
| 6,862,709 B2 * | 3/2005 | Takiguchi et al. ......... 715/500.1 |
| 2001/0041347 A1 * | 11/2001 | Sammak et al. ............ 435/7.23 |
| 2003/0065260 A1 * | 4/2003 | Cheng et al. ................ 600/427 |
| 2003/0065526 A1 * | 4/2003 | Giacchetti et al. .............. 705/1 |
| 2005/0281446 A1 * | 12/2005 | Glukhovsky et al. ........ 382/128 |
| 2006/0193505 A1 * | 8/2006 | Glukhovsky et al. ........ 382/128 |

* cited by examiner

*Primary Examiner*—Tom Y Lu

(57) ABSTRACT

A system and method are provided for simplifying off-line quantification of ultrasound images by displaying a graphical user interface showing a real-time ultrasound image for enabling a user to freeze the real-time ultrasound image to display an image sequence capable of being modified and played back by the user. The graphical user interface displays graphs or curves providing data related to the ultrasound images. Each data point on the curves represents one ultrasound image of the ultrasound images. When the user selects a particular data point on a curve of a graph, the corresponding ultrasound image is displayed by the graphical user interface. The user can then select another data point on the same curve or another curve to display another corresponding ultrasound image. The two ultrasound image framescan then be compared. The system and method of the present invention further provide the ability for a user to select a region of interest within one of the displayed images to display parameters associated with the selected region of interest for the two ultrasound images.

10 Claims, 3 Drawing Sheets

SYSTEM AND METHOD FOR COMPARING ULTRASOUND IMAGES CORRESPONDING TO TWO USER-SELECTED DATA POINTS

FIELD OF THE INVENTION

The present invention relates generally to ultrasound image quantification and more specifically to a system and method for comparing ultrasound images corresponding to two user-selected data points.

BACKGROUND OF THE INVENTION

Traditionally quantitative analysis of ultrasound image data has been performed online, i.e., on the ultrasound system itself. Because of the limitation of performing complex analyses within the clinical workflow, quantification has been limited to two-dimensional x-y data such as areas and lengths, and the analysis of Doppler waveforms. This is due primarily, to limited computational speed of the acquisition/display system and patient workflow management. More recently, complex analysis and measurements have been developed for off-line workstations. Current developments in computational speed are allowing the user to access more complex quantitative analysis both on-line and off-line (e.g. at a PC workstation) in a timely manner. The clinical practice is moving away from just anatomical imaging, to imaging methods which provide functional assessment. This information may be quantitative in nature, which gives the clinician access to physiological data in the management of their patients. These users will require tools to assist them in analyzing this information in a time-efficient and reproducible manner.

Despite the increase in computational power to perform more complex analyses on ultrasound images, there is still the need for user interaction with the ultrasound image data. Ultrasound images are typically stored in movie form, called "CINELOOP™ sequences". Since ultrasound is an inherently real-time imaging modality, CINELOOP™ frame rates are typically in excess of 30 Hz (30 frames/second). Therefore, even a modest 10 second CINELOOP™ contains over 300 image frames.

Accordingly, there exists a need for enabling a user to interact with the ultrasound image data. Specifically, a need exists for displaying two ultrasound images of a CINELOOP™ sequence, where each corresponds to a particular user-selected data point on the same graph or different graphs, for comparison purposes. A need further exists for selecting a region of interest with respect to the two displayed images and displaying parameters associated with the selected region of interest for the two ultrasound images for comparison purposes.

SUMMARY

An aspect of the present invention is to provide a system and method for comparing ultrasound images corresponding to two user-selected data points on the same graph or different graphs for comparison purposes.

In a preferred embodiment of the present invention, a system and method are provided for simplifying off-line quantification of ultrasound images by displaying a graphical user interface showing a real-time ultrasound image for enabling a user to freeze the real-time ultrasound image to display an image sequence capable of being modified and played back by the user. Upon freezing the real-time image, the graphical user interface displays a tagging system having a corresponding identification tag for each ultrasound image of the image sequence.

The graphical user interface further displays graphs or curves providing data related to the ultrasound images. Each data point on the curves represents one ultrasound image frame of the ultrasound image sequence. When the user selects, e.g., by clicking using a mouse, a particular data point on a curve of a graph, the corresponding ultrasound image is displayed by the graphical user interface. The user can then select another data point on the same curve or another curve to display another corresponding ultrasound image. The two ultrasound images can then be compared. The system and method of the present invention further provide the ability for a user to select a region of interest within one of the displayed images to display parameters associated with the selected region of interest for the two ultrasound images. The parameters can then be compared. It is provided that a tool tip box or a window appears on the graphical user interface upon selection of the region of interest. The tool tip box includes delta values for the two sets of parameters at the region of interest for comparison purposes.

The system and method of the present invention are embodied by at least one software module having a series of programmable instructions capable of being executed by a processor for performing its respective functions. The software module includes a series of programmable instructions for enabling a user to select two data points on a curve and for displaying the ultrasound images corresponding to the two user-selected data points. The series of programmable instructions further enable the user to select a region of interest and to display parameters associated with the selected region of interest for the two ultrasound images. Additionally, the series of programmable instructions further enable the generation and display of a tool tip box or a window which includes delta values for the two sets of parameters at the region of interest.

The software module is preferably stored within a memory storage device, such as a computer hard drive, within a memory module, such as a RAM or ROM module, and/or on a computer readable medium, such as a CD-ROM, and is capable of being accessed for execution by the processor. The software module is preferably incorporated within a software quantification tool for use in off-line image review, quantification and interpretation of ultrasound images and other related data.

BRIEF DESCRIPTION OF THE FIGURES

Various embodiments of the invention will be described herein below with reference to the figures wherein.

DETAILED DESCRIPTION OF THE PREFERRED EMBODIMENTS

Figure 1:
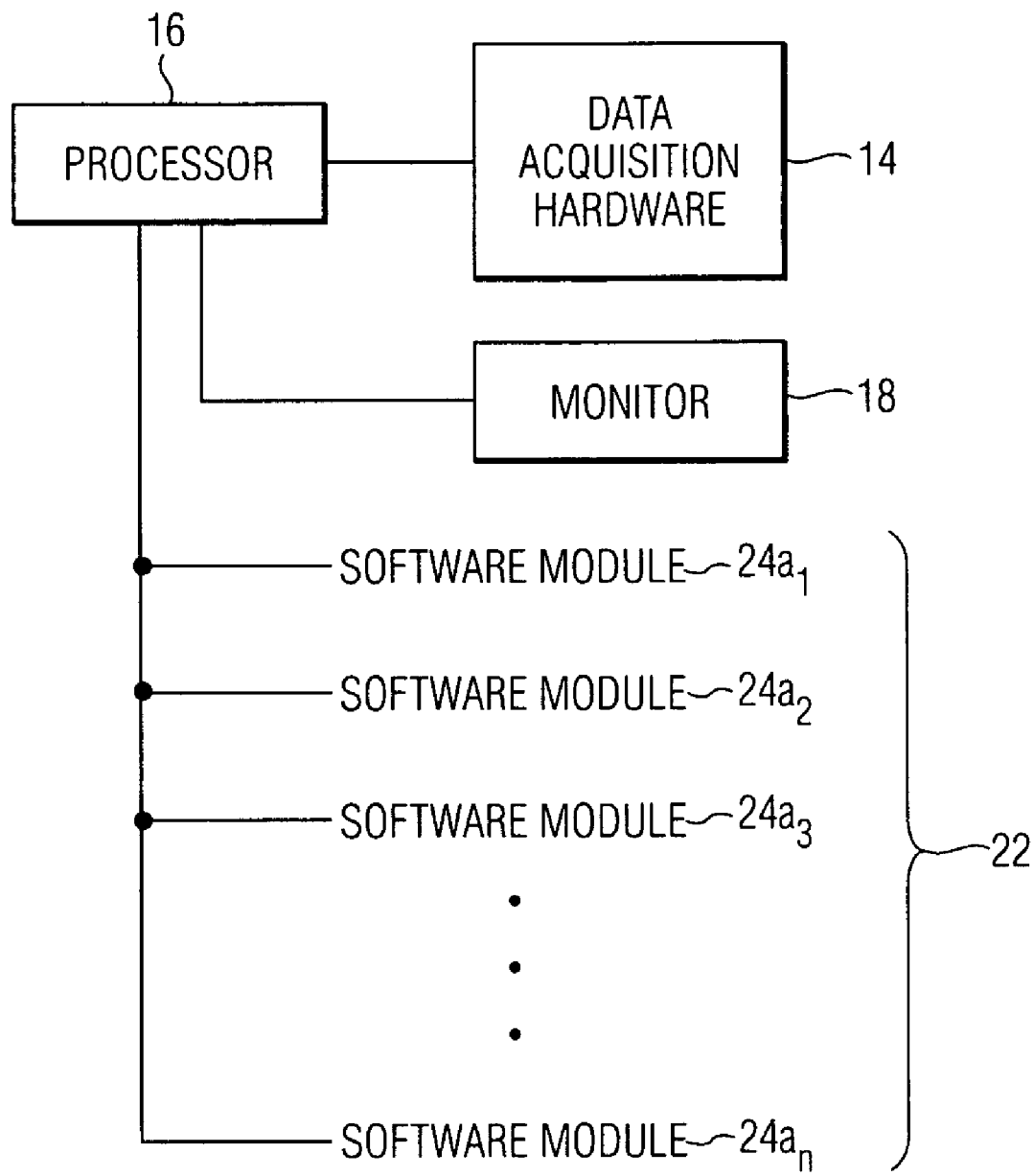
FIG. 1 is a block diagram of the system according to the present invention.

With reference to FIG. 1, there is shown a block diagram of a system according to the present invention and designated generally by reference numeral 10. The system 10 includes an ultrasound imaging system 12, such the SONOS™ 5500 digital echocardiography system or an HDI 5000 system available from Philips Medical Systems, for acquiring and storing ultrasound images. Another embodiment of the system includes an off-line PC workstation capable of reviewing and quantifying the image data acquired on the ultrasound system. The system 12 includes data acquisition hardware 14, such as an ultrasonic transducer and a keyboard, a processor 16 for processing the data, and a monitor 18 capable of displaying a graphical user interface 20 (see FIG. 2) of a software quantification tool. The graphical user interface 20 displays the acquired ultrasound images to a user, as well as other information.

The system 10 further includes operational software 22 capable of being executed by the processor 16 of the ultrasound imaging system 12 for performing the various functions of the imaging system 12, such as ultrasound image acquisition and harmonic image enhancement. The operational software 22 includes a plurality of software modules $24a_1$-$24a_n$ or plug-ins for performing the various functions, including the functions and features of the present invention.

The plurality of software modules $24a_1$-$24a_n$ are preferably stored within a memory storage device, such as a computer hard drive, within a memory module, such as a RAM or ROM module, and/or on a computer readable medium, such as a CD-ROM, and are capable of being accessed for execution by the processor 16. The plurality of software modules $24a_1$-$24a_n$ are preferably incorporated within the software quantification tool for use in off-line image review, quantification and interpretation of ultrasound images and other related data.

Figure 2:
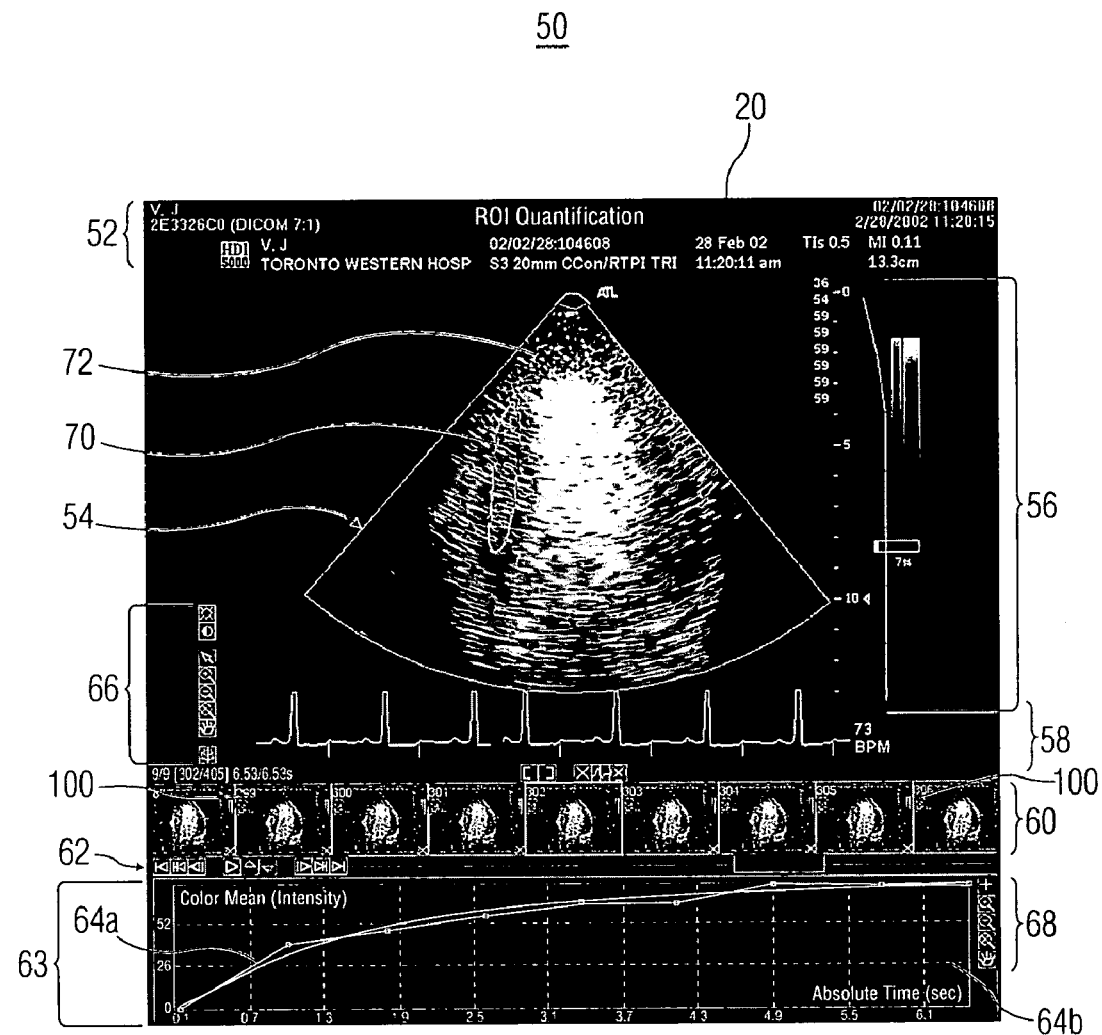
FIG. 2 is a screen view of a graphical user interface capable of being displayed by the system of FIG. 1.

With reference to FIG. 2, there is shown an exemplary screen 50 of the graphical user interface 20. The screen 50 includes time, patient and other data 52 on a top portion, a large frozen or paused playback image 54 of the myocardium, a vertical scale 56 along the right side of the image 54, a bits per minute (BPM) signal 58 below the image 54, a CINELOOP™ thumbnail display 60, image review control soft buttons 62 (e.g., reverse, forward and play/pause, speed control, jump to first frame, frame step forward, jump to image of interest forward, jump to last frame, frame step backward, jump back to image of interest), a graph 63 displaying time intensity and one-minus-exponential curves 64a, 64b below the CINELOOP™ image 60, a first group of soft buttons 66 for at least adjusting the contrast of the image 54, selecting at least one region of interest (ROI) on the image 54, enlarging the image 54, moving the image 54, and zooming in and out with respect to the image 54, and a second group of soft buttons 68 for at least adjusting the position of the graph 63 displaying the curves 64a, 64b, and zooming in and out with respect to the graph 63 displaying the curves 64a, 64b.

In order to obtain the screen 50 of FIG. 2, the user freezes or pauses the large playback image 54 which is being played in real-time by clicking on the image 54 or by some other method. Upon freezing the large playback image 54, the frozen image frame and those preceding and following it are shown in a thumbnail sequence 60, below the frozen image 54, as shown by FIG. 2. The border of the image which corresponds to the large playback image 54 is highlighted in the thumbnail display 60.

Each thumbnail corresponds to a respective image of the CINELOOP™ sequence 60 and is tagged by a respective tag of a tagging system. The tagging system primarily includes a plurality of tags 100 or reference numerals identifying each image of the CINELOOP™ sequence 60. The plurality of tags 100 are embodied within the system 12 as a data structure, such as a top-down stack or a sequence of objects connected by pointers.

Each tag or reference numeral is positioned on the top left portion of each image. The images are tagged or numbered consecutively in the image sequence 60. In the exemplary screen 50, the image of the CINELOOP™ sequence 60 identified by numeral 302 corresponds to the large playback image 54.

Two regions of interest 70, 72 are shown on the exemplary screen 50 as defined and selected by the user. The regions of interest 70, 72 are preferably selected by the user using an ROI software module which is preferably one of the plurality of software modules $24a_1$-$24a_n$. The time intensity curves and one-minus-exponential curves 64a, 64b are fit by the quantification tool to the ROI data corresponding to the two selected regions of interest 70, 72, respectively.

The system 10 of the present invention includes a compare image mode software module $24a_1$ which includes a series of programmable instructions for enabling the user to select two data points on a graph and for displaying the ultrasound images corresponding to the two user-selected data points. The series of programmable instructions further enable the user to select a region of interest and to display parameters associated with the selected region of interest for the two ultrasound images. Additionally, the series of programmable instructions further enable the generation and display of a tool tip box or a window which includes delta values computed by the compare image mode software module $24a_1$ for the two sets of parameters at the region of interest.

Figure 3:
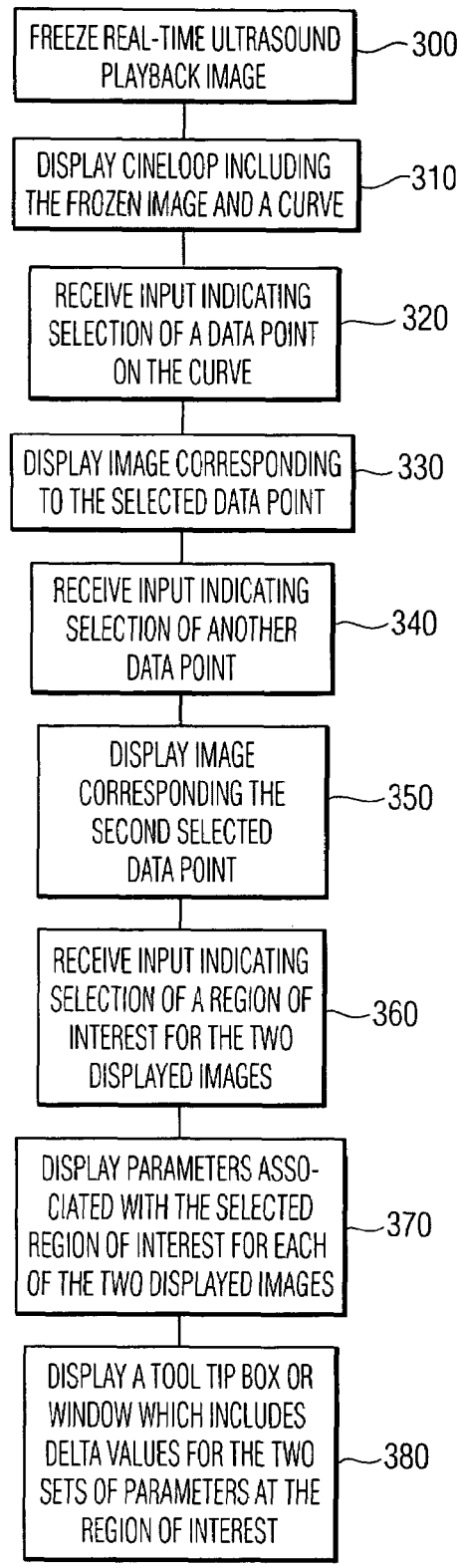
FIG. 3 is an operational flow block diagram illustrating a method of operation according to the present invention.

With reference to FIG. 3, there is shown an operational flow block diagram of the method of operation of the compare image mode software module $24a_1$ for selecting data points on one or more curves to display the corresponding ultrasound images on the graphical user interface 20 according to the present invention.

With reference to FIG. 3, the system 10, in step 300, accepts an input from a user to freeze a real-time ultrasound image being displayed by the graphical user interface 20 of the ultrasound imaging system 12. In step 310, a CINELOOP™ image sequence 60 is displayed which includes the frozen image and at least one time intensity curve plotted on a graph. In step 320, the system 10 receives an input from the user indicating selection of a data point on a curve of the at least one curve. In step 330, the ultrasound image frame corresponding to the selected data point in step 320 is displayed. In step 340, the system 10 receives another input from the user indicating selection of another data point on the same or another curve of the at least one curve. In step 350, the ultrasound image frame corresponding to the second selected data point in step 340 is displayed.

In step 360, the system 10 receives an input from the user indicating selection of a region of interest for the two displayed ultrasound images. In step 370, the system 10 displays on the graphical user interface 20 the parameters associated with the selected region of interest for each of the two ultrasound images. In step 380, the system 10 automatically displays a tool tip box or a window which includes delta values for the two sets of parameters at the region of interest.

Although the preferred embodiment is related to a system for the review, editing, analysis and storage of ultrasound images, the same tools described above for performing the various functions are relevant to any medical imaging modality that uses real-time data for quantification. Examples of such modalities are X-ray, Computed Tomography, Magnetic Resonance Imaging, and Digital Angiography.

What has been described herein is merely illustrative of the principles of the present invention. For example, the system and method described above and implemented as the best mode for operating the present invention are for illustration purposes only. Other arrangements and methods may be implemented by those skilled in the art without departing from the scope and spirit of this invention.

We claim:

1. An imaging system for accessing an image using at least one graph comprising:
   a display displaying the at least one graph having at least one curve plotted thereon, each of a plurality of data points of the at least one curve corresponding to a different image;
   means for receiving an input indicating selection by a user of a data point of the plurality of data points and for displaying a fist image corresponding to the selected data point on the display, wherein the means for receiving is configured to receive another input indicating selection by the user of a subsequent data point of the plurality of data points and is configured to display a second image corresponding to the subsequently-selected data point on the display
   means for receiving a selection by a user of a portion of one of the first and second images indicating a common region of interest for the first and second images; and
   means for displaying two sets of parameters for the user selected region of interest, each set of parameters corresponding to one of the first and second images.

2. The system according to claim 1, further comprising means for displaying a window including delta values for the two sets of parameters on the display.

3. An imaging system for displaying parameters associated with a region of interest common to two different images, the system comprising:
   means for receiving an input indicating selection of a portion of one of the two different images by a user indicating a user selected region of interest common to the two different images; and
   a display for displaying a first set of parameters associated with the user selected region of interest for one of the two different images and a second set of parameters associated with the user selected region of interest for the other of the two different images.

4. The system according to claim 3, further comprising means for accessing the two images using at least one graph, wherein the means for accessing comprises:
   means for displaying the at least one graph having at least one curve plotted thereon on the display, each of a plurality of data points of the at least one curve corresponding to an image;
   means for receiving an input indicating selection by a user of a data point of the plurality of data points and displaying an image corresponding to the selected data point on the display, wherein the displayed image is one of the two images; and
   means for receiving another input indicating selection by the user of a subsequent data point of the plurality of data points and displaying another image corresponding to the subsequently-selected data point on the display, wherein the displayed image is the other of the two images.

5. The system according to claim 4, further comprising means for displaying a window including delta values for the two sets of parameters on the display.

6. A computer-readable medium storing a series of programmable instructions for performing a method for displaying parameters associated with a region of interest common to two different images, the method comprising the steps of:
   receiving an input indicating selection of a portion of one of the two different images by a user indicating a user selected region of interest common to the two different images;
   displaying a first set of parameters associated with the user selected region of interest for one of the two different images; and
   displaying a second set of parameters associated with the user selected region of interest for the other of the two different images.

7. The computer-readable medium according to claim 6, wherein the method further comprises the step of accessing the two images using at least one graph prior to the receiving step, wherein the step of accessing comprises the steps of:
   displaying the at least one graph having at least one curve plotted thereon, each of a plurality of data points of the at least one curve corresponding to an image;
   receiving an input indicating selection by a user of a data point of the plurality of data points;
   displaying an image corresponding to the selected data point, wherein the displayed image is one of the two images;
   receiving another input indicating selection by the user of a subsequent data point of the plurality of data points; and
   displaying another image corresponding to the subsequently-selected data point, wherein the displayed image is the other of the two images.

8. The computer-readable medium according to claim 6, further comprising the step of displaying a window including delta values for the two sets of parameters.

9. A computer-readable medium storing a series of programmable instructions for selecting a region of interest comprising the steps of:
   displaying a first image corresponding to a first selected data point of a plurality of data points
   displaying a second image corresponding to a second selected data point
   receiving an input correspond to one of the first and second images from the user indicating user selection of a region of interest less than an entire image that is common to each of the first and second displayed images;
   displaying two sets of parameters for the user selected region of interest, each set of parameters corresponding to one of the first and second displayed images.

10. The computer-readable medium according to claim 9, wherein the method further comprises the step of displaying a window including delta values for the two sets of parameters.

* * * * *